(12) United States Patent
Smith

(10) Patent No.: US 8,418,872 B2
(45) Date of Patent: Apr. 16, 2013

(54) STERILIZATION CONTAINER WITH RELEASABLE AND PERMANENT LOCK

(75) Inventor: Tara Denise Smith, Marietta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 106 days.

(21) Appl. No.: 12/974,422

(22) Filed: Dec. 21, 2010

(65) Prior Publication Data

US 2012/0152957 A1 Jun. 21, 2012

(51) Int. Cl.
*B65D 35/14* (2006.01)

(52) U.S. Cl.
USPC ...... 220/495.01; 220/784; 220/788; 292/304; 292/DIG. 11

(58) Field of Classification Search .... 220/23.87–23.88, 220/315, 324, 326, 345.2, 495.01, 784, 788, 220/831–832; 206/439, 807, 1.5
See application file for complete search history.

(56) References Cited

U.S. PATENT DOCUMENTS

| | | | |
|---|---|---|---|
| 4,105,407 A | 8/1978 | Sanderson | |
| 4,671,943 A | 6/1987 | Wahlquist | |
| 4,730,726 A | 3/1988 | Holzwarth | |
| 4,754,595 A | 7/1988 | Sanderson | |
| 4,774,063 A | 9/1988 | Runnells | |
| 4,783,321 A | 11/1988 | Spence | |
| 4,798,292 A | 1/1989 | Hauze | |
| 4,854,459 A * | 8/1989 | DeJonge | 215/220 |
| 4,915,913 A | 4/1990 | Williams et al. | |
| 5,066,290 A | 11/1991 | Measells et al. | |
| 5,518,115 A * | 5/1996 | Latulippe | 206/370 |
| 5,829,588 A | 11/1998 | Bloomfield | |
| 5,922,428 A * | 7/1999 | Pufahl | 428/42.1 |
| 6,077,485 A * | 6/2000 | Baker | 422/300 |
| 6,319,481 B1 * | 11/2001 | Banks | 422/300 |
| 6,426,041 B1 | 7/2002 | Smith | |
| 6,589,477 B1 * | 7/2003 | Frieze et al. | 422/22 |
| 6,715,628 B1 | 4/2004 | Nichols et al. | |
| 7,032,752 B2 | 4/2006 | Krackow | |
| 7,600,639 B2 | 10/2009 | Japuntich et al. | |
| 7,914,751 B2 * | 3/2011 | Oertmann | 422/297 |
| 2002/0192108 A1 | 12/2002 | Wu | |
| 2003/0080571 A1 | 5/2003 | Schainholz et al. | |
| 2004/0040967 A1 * | 3/2004 | Eiskant et al. | 220/324 |
| 2004/0073177 A1 | 4/2004 | Hickle | |
| 2004/0256270 A1 * | 12/2004 | Gleichauf et al. | 206/439 |
| 2005/0033430 A1 | 2/2005 | Powers et al. | |
| 2007/0054117 A1 * | 3/2007 | Katchko et al. | 428/346 |
| 2007/0095699 A1 | 5/2007 | Frieze et al. | |

FOREIGN PATENT DOCUMENTS

| | | |
|---|---|---|
| WO | WO 95/05981 A1 | 3/1995 |
| WO | WO 03/043666 A1 | 5/2003 |

OTHER PUBLICATIONS

Co-pending U.S. Appl. No. 12/974,391, filed Dec. 21, 2010, by Smith for "Disposable Sterilization Liner with Lid."

* cited by examiner

*Primary Examiner* — Mickey Yu
*Assistant Examiner* — Brijesh V Patel
(74) *Attorney, Agent, or Firm* — James B. Robinson

(57) ABSTRACT

A container for sterilizing and storing surgical materials and preserving surgical materials in a sterilized condition is provided. The container can include a lid and tray that may be used to contain an instrument basket for sterilization. The container has a lock that releasably holds the lid and tray together and that can rotate into a second position, after it is released, and non-releasably lock into the second position.

10 Claims, 3 Drawing Sheets

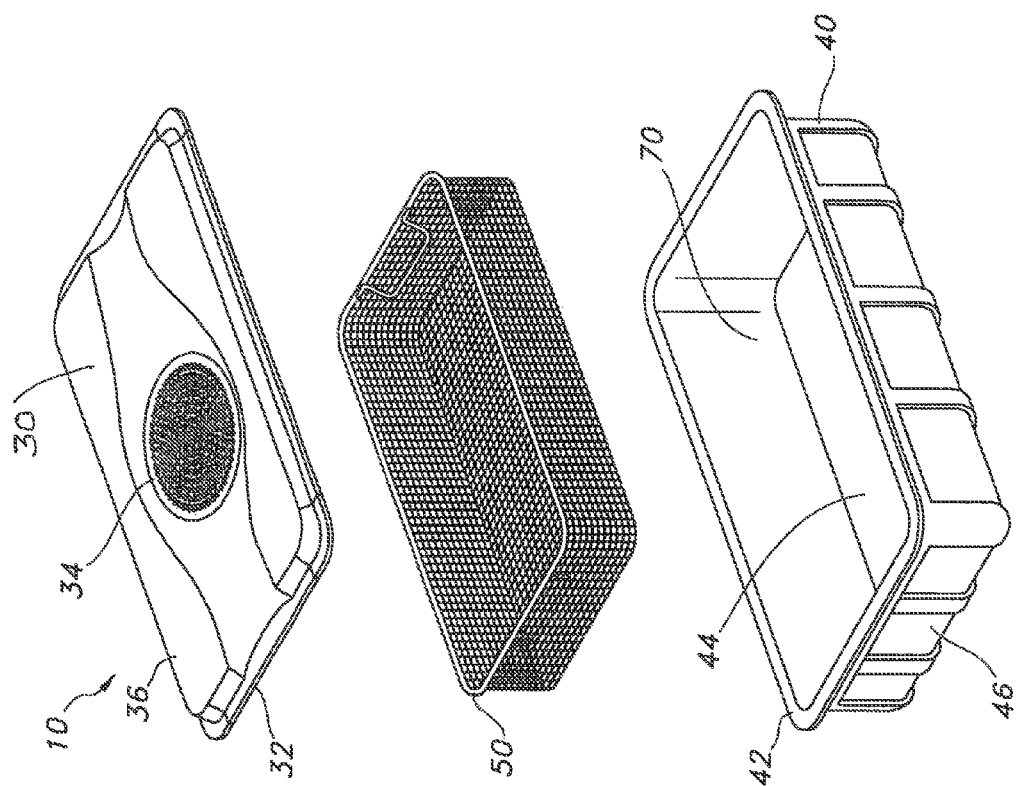

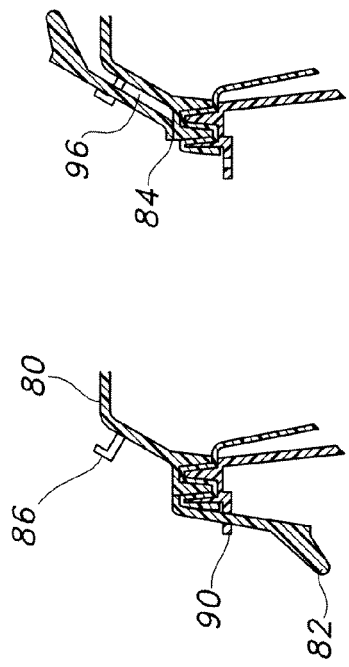
FIG. 3A
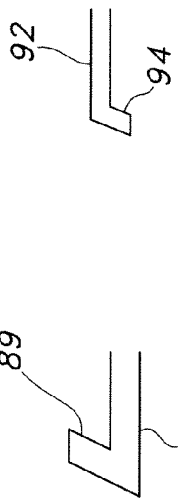
FIG. 3B
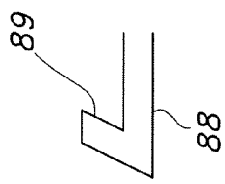
FIG. 4
FIG. 5
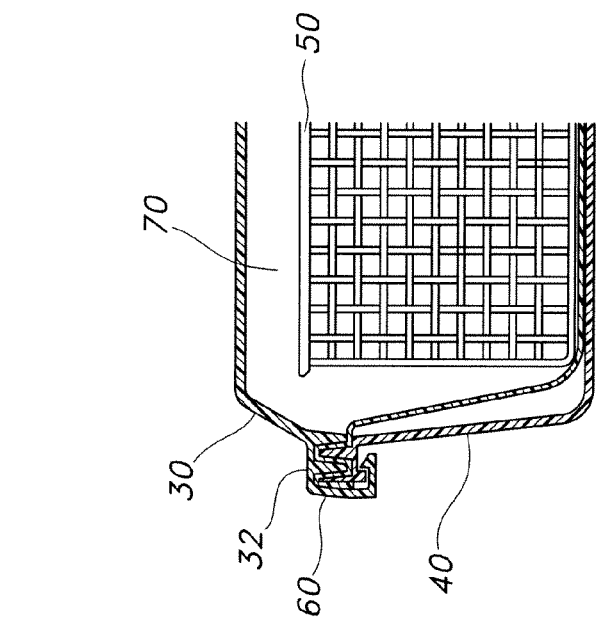
FIG. 2

STERILIZATION CONTAINER WITH RELEASABLE AND PERMANENT LOCK

Medical equipment is sterilized prior to surgical use in order to avoid harmful and infectious microbes being introduced to patients. There are two generally available methods of performing sterilization of medical equipment. One of the methods involves the use of a "sterilization wrap" fabric and the other uses a sterilization container into which the instruments are placed.

Sterilization wrap is used by enveloping the medical equipment with the wrap, which is generally made of a gas permeable material like a non-woven fabric. Examples of such wraps may be found in U.S. Pat. No. 6,406,674, which describes a wrap of two layers bonded in such a way as to remain visibly two layers to a casual viewer. This wrap is superior to single layer wraps as it provides greater resistance to wear and tear.

Regarding sterilization wraps; sterilization wraps are made of a relatively thin, flexible material and have low initial cost and are typically disposable, i.e., discarded after a single use. Items to be sterilized are usually placed within a metal sterilization tray prior to wrapping the items with sterilization wrap. These sterilization trays have pointed edges or other features that may concentrate forces and generate very small tears or snags if the wrap contacts them. When wrapped trays are transported on carts or stacked prior to sterilization or after sterilization, other sources of very small tears or breaches in the barrier may develop in the wrap due to pressure or impact. These tears may allow contaminates to reach the items. The result is added expense because the items need to re-handled, re-wrapped and re-sterilized.

In addition, because sterilization wraps are not transparent, the medical professional cannot visually inspect the items within the wrap for content or for assurance that the sterilization procedure has been completed. This can lead to a medical professional opening the wrong sterilization tray during a procedure and/or lead to lack of confidence that the tray is truly sterilized. As a result, trays and articles may require unnecessary re-handling and re-sterilization, wasting time and money.

Rigid sterilization containers are generally rectangular boxes having a bottom and top or lid. Items to be sterilized, e.g. medical instruments, are placed in the container or more particularly into a standard metal hospital basket, which is then placed into the container. The container is then placed in a sterilization device for a time certain to kill any bacteria or other microorganisms inside it. The rigid sterilization containers are generally reusable and so the hospital must have a process and facilities for cleaning the containers, storing them between uses, and returning them to the proper place for reuse. These containers must also be checked for wear and damage on a reasonable basis to ensure proper sterilization and that the sterilized items remain sterile until they are needed for a surgical procedure.

Reusable vented rigid sterilization containers, although generally effective, are locked closed prior to sterilization and cannot be reopened once locked except through the breaking of the lock. These locks are generally of a metallic or plastic one-way "tie" type of lock that has a built in ratcheting construction that cannot be undone except through the use of a destructive amount of force or through cutting of the tie material. If, prior to sterilization, a user wants to double check the contents of the container or add or subtract another item, the lock must be broken and replaced prior to sterilization. This is inefficient and wasteful.

During the sterilization process, the sterilization wrapped items or sterilization containers are placed into a sterilization chamber and the gas permeable material in the sterilization wrap or the vents of the sterilization container allow a gaseous sterilant to contact the equipment to be sterilized. The most common gases for sterilization are steam and ethylene oxide, so the wrap or container must be constructed of materials that are stable under the conditions of steam sterilization; e.g. resistant to high temperature and moisture and stable when exposed to ethylene oxide gas.

Although utilization of sterilization wrap and/or use of vented rigid reusable sterilization containers are generally effective, there are certain disadvantages associated with each of these techniques. As noted above, wraps may suffer from difficult to find cuts and tears that may render them ineffective and which may provide a pathway for microorganisms to re-enter the instrument basket after sterilization. Rigid vented sterilization containers are generally not transparent and are locked shut once the instruments are placed inside, making visual inspection and instrument content checking impossible without breaking open the container and repacking and re-sterilizing it.

Thus, there remains a need in the art for a procedure to check the contents of a package to be sterilized to ensure that the proper instruments are inside without breaking the container open. What is needed is sterilization containers that are economical and that can be opened repeatedly prior to sterilization if desired, to check the contents and add another item.

SUMMARY

The present disclosure provides a lock for securing a container. The lock has three locking elements, the first locking element is located on a first piece and has a hinge adapted to releasably engage a second locking element located on a second piece. The first locking element can also non-simultaneously, non-releasably engage a third locking element located on the first piece.

The lock may be used on a container for sterilizing and preserving surgical materials in a sterilized condition. In some embodiments the container may have a tray and lid with a central portion with a permeable filter and a continuous lip. In other embodiments the tray may be replaced with a reusable frame and a disposable polymeric liner.

The permeable filter provides a path for a sterilant to enter the container from outside the container and for maintaining aseptic conditions inside the container after sterilization. The permeable filter should allow the passage of gases such as those commonly used in sterilization, for example, steam and ethylene oxide. The filter must allow for the passage of air after sterilization is complete so that any moisture may be allowed to exit the container as water vapor. Air must also be allowed to enter the container after sterilization to allow for the contraction of the air inside the container during steam sterilization as it cools.

The gas permeable filter is desirably in the central portion of the lid. The filter allows the gas used for sterilization to enter the container and sterilize the instruments inside. The filter material may be medical grade paper, polyolefin meltblown materials and nonwoven laminate materials such as laminates of spunbond materials and meltblown materials. The gas permeable filter material should be permeable to water vapor and have a minimum water vapor transmission rate (WVTR) of about 200 $g/m^2/16$ hours, calculated in accordance with ASTM Standard E96-80.

In those embodiments using a tray, the lid is designed to mate with the tray that has a base, sides and a continuous rim.

The tray is designed to receive a basket for containing surgical instruments. The tray lip and lid rim together form a barrier to inhibit the passage of microorganisms into the chamber. In this embodiment the lid and tray are the first and second pieces, respectively and the lock has a hinge for releasably securing the lid and tray together in a first locked position. The lock may be non-releasably locked in a second lock position that does not secure the lid to the tray.

The lid is desirably disposable, i.e., designed for a single use, and may be made from inexpensive materials like plastics and common metals like polypropylene, polyethylene, polyesters, thermoplastic polyurethanes, olefinic copolymers, aluminum, copper and various alloys. In the embodiments with a frame and liner, the liner is desirably disposable also.

In still another embodiment, the rim of the lid or tray may include a material that is heat activated during steam sterilization to secure the lid to the tray. Such materials include hot melt adhesives made from polyolefins, block copolymers, resins, waxes and combinations thereof, that have a melting point below 270° F. (132° C.).

Engaging the releasable lock components relies on the initial spatial deflection of at least one element of a lock component. These may be, for example, a bayonet tab with a detent engaging against a mating element of the other lock component, followed by spatial re-deflection of the at least one element so that it 'catches' one or more elements of the other lock component. The detent and mating component are adapted to be releasable by making the detent relatively small so that the amount of force required to release it from the mating feature is concomitantly small. The mating component may be a bar or the edge of an opening into which the bayonet tab can protrude.

Alternative methods of releasably connecting the first and second locking elements include, for example, the use of balls and sockets wherein a ball component will mate with a socket that is slightly smaller than the diameter of the ball. Like the tab and detent system, the application of manual force to urge the ball into the socket will deform one or both components and allow them to pass beyond one another to a first locking position.

The locking elements may be arranged along the outer edge of the lid and tray and may be between a centimeter in length, to quite large, e.g. 10 cm or more. In the case of a large sterilization container, multiple large locks may deployed along each side to help to ensure that the barrier between the lid and tray does not become ruptured or damaged and allow the passage of microorganisms into the container.

When the lock is moved to its final, locking position with the second and third locking elements engaged, a space is created between the engaged locking elements and the lid or tray. The space may be varied in size by the proper sizing of the locking elements and provides a handle for manual manipulation of the lid or tray.

BRIEF DESCRIPTION OF DRAWINGS

FIG. 1 is an illustration showing an exploded view of an exemplary locking sterilization container.

FIG. 2 is an illustration showing a cross-sectional view of an exemplary locking sterilization container.

FIGS. 3A and 3B are cross-sectional views of a two position lock that allows a releasable or non-permanent lock between the lid and tray and a permanent lock between the flap and first locking feature.

FIG. 4 is a cross-sectional view of a bayonet tab with a detent that may be used as the second locking element of the releasable lock.

FIG. 5 is a cross-sectional view of a bayonet tab with a detent that may be used as the first locking element of the non-releasable lock.

DETAILED DESCRIPTION

Figure 6:
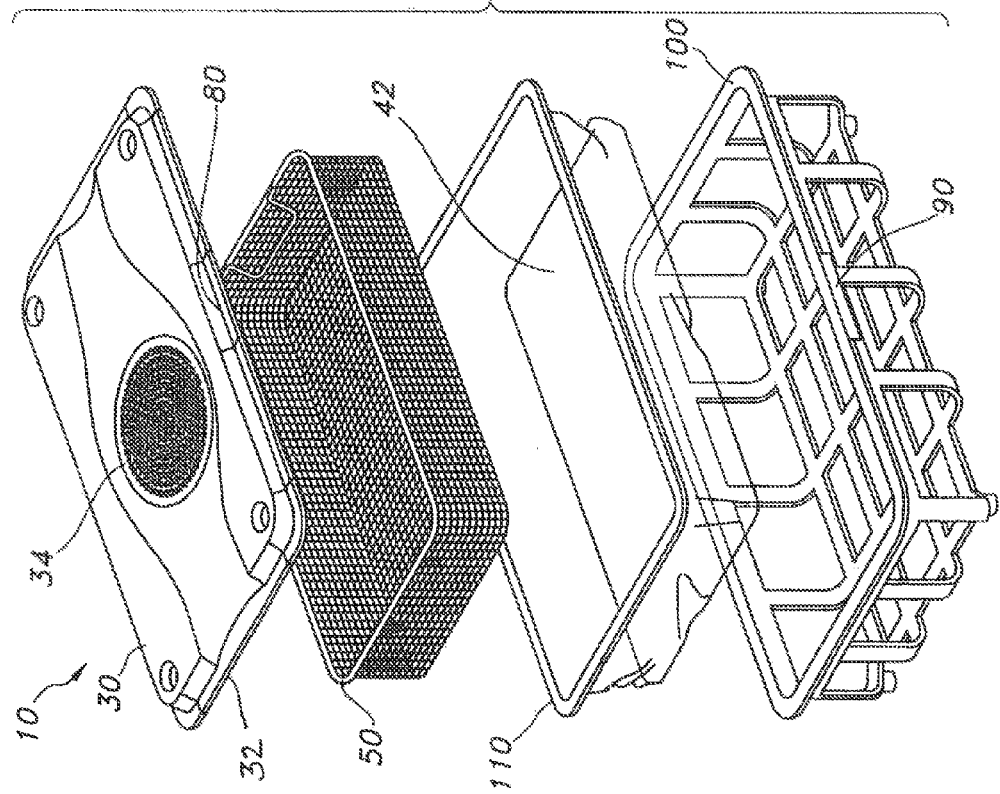
FIG. 6 is an illustration showing an exploded view of another embodiment of a locking sterilization container.

The present disclosure provides a locking container for sterilizing and storing surgical materials and aseptically opening and aseptically preserving surgical materials in a sterilized condition. These containers offer an increased level of confidence of the sterility of the contents while allowing a user to open the container prior to sterilization to check the contents to ensure that the proper instruments are present in the container. This functionality also allows a user to add an item that may be needed for a specialized surgery or to subtract an extra item that is not needed for a particular surgery.

The disclosure will be described with reference to the following description and figures which illustrate certain embodiments. It will be apparent to those skilled in the art that these embodiments do not represent the full scope of the disclosure which is broadly applicable in the form of variations and equivalents as may be embraced by the claims appended hereto. Furthermore, features described or illustrated as part of one embodiment may be used with another embodiment to yield still a further embodiment. It is intended that the scope of the claims extend to all such variations and embodiments.

Referring now to FIG. 1, there is illustrated an exemplary locking sterilization io container 10 having a lid 30 and a tray 40 that are adapted to mate together at lid 30 rim 32 and tray 40 lip 42. Most embodiments of the locking sterilization container lid 30 include a permeable filter 34. The tray 40 is sized so that it may accept a standard hospital instrument basket 50. Trays may be produced in various sizes, not merely a single size, since there is a variety of surgeries and the instruments required for each are different. Some relatively simple surgeries require few instruments to be sterilized and so can use a smaller tray, while more complicated surgeries require more instruments and so also require larger or multiple, trays. The lid 30 generally includes a central portion 36 and a rim 32. The lip 42 of the tray 40 forms or includes an upper portion of a barrier 60 to inhibit the passage of microorganisms from the unsterile exterior environment to the internal, sterile environment of the container. When the lid 30 and the tray 40 are mated together, they enclose a chamber 70 for containing the surgical materials. The chamber is generally rectangular in shape though other shapes are possible provided the lid and tray can be mated together sufficiently to provide the barrier necessary to maintain sterility after the sterilization procedure.

In the use of the container, the lid 30 is placed on the tray 40 in a face-to-face mating arrangement such that the lid is snugly maintained in position on the tray. Once in this face-to-face arrangement, the lip 42 of the tray 40 and the rim 32 of the lid 30 function as a gasket between the lid 30 and tray 40, to desirably seal the sterilization container and keep contaminants out of the container. When the lip and rim are properly secured together by, for example, the locking mechanism described herein, they form a barrier 60 to inhibit the passage of microorganisms into the chamber 70 between the lid 30 and the tray 40. The barrier 60 desirably defines a tortuous path from the outside of the container to the chamber 70 to inhibit the passage of microorganisms as illustrated in FIG. 2 and described above. Alternatively, the lip and rim may function as a seal between the lid 30 and tray 40 to produce a barrier 60 to inhibit the passage of microorganisms. This barrier may use a seal that may be provided by various materials or mechanisms such as, for example, a gasket, pliable io material and/or heat sensitive material that is adapted to melt, deform or otherwise change shape to block to the passage of microorganisms between the lid 30 and tray 40 in to the chamber 70. The gasket material may be provided by, for example, a single or double sided adhesive tape that may be provided in the room where the containers are prepared for sterilization. The tape may be of the proper width, e.g. about the same size as the rim 32 so that it may be easily adhered to the rim by a user using minimal skill in a relatively rapid procedure. In one embodiment, a single sided tape with a gasket may be used, with the adhesive side being adhered to the rim and the gasket material facing the lid. The gasket material need not be particularly thick as the lid and rim should mate together relatively snugly. The gasket material may be for example, between 2 and 8 mm in thickness, more particularly about 4 mm in thickness.

The lid 30 desirably also comprises a permeable filter 34. The permeable filter 34 provides a path for a sterilant to enter the chamber 70 from outside the container 10 in order to sterilize the contents of the chamber. The permeable filter 34 also maintains aseptic conditions inside the chamber 70 after the sterilization process has been completed by allowing gases such as air to enter or exit the chamber without allowing passage of microorganisms. This is important in procedures using steam sterilization, for example, since after sterilization the contents of the container will be hot and the container will also contain moisture from the condensation of the steam that was used to sterilize the contents of the container. The permeable filter will allow the exchange of air between the inside and outside of the container. This will permit air to enter and fill the container as the contents cool, so that the sides of the container do not distort inwardly due to the lower pressure inside the container caused by the cooling of the air after removal of the steam. Distortion of the container could cause a failure of the gasket between the tray and lid leading to contamination by microorganisms and loss of sterility. Allowing air to be exchanged between the container and the outside environment also allows the escape of moisture from the container in the form of water vapor, especially if the container is stored in a room having relative humidity lower than that of the environment where the sterilization was performed.

The permeable filter 34 is desirably located in the central area of the lid 30 and contains one or more openings and/or passages between the outside of the container 10 and the chamber 70. The permeable filter 34 may, however, be located in other portions of the lid 30. The filter 34 may also be located on other portions of the container exclusive or inclusive of the lid. The permeable filter may be located, for example, on the side of the tray. There may be more than one filter located, for example, on opposite sides or ends of the tray and arrange in a pairing of filters opposite one another. The filter may be located on the bottom of the tray although such a location risks damage to the filter as the container is moved and stored after sterilization. Generally, however the exact location of the permeable filter is not critical as long as it is present and functional.

The permeable filter may be a conventional filter material used for sterilization container applications and should be inexpensive enough to be discarded or recycled after a single use. The successful filter materials should be those that are stable in the presence of steam and high heat, as well as those that are chemically stable such that they are unaffected by ethylene oxide and other common chemical sterilizing media. It is also desirable that filter materials be sufficiently durable so that they are not easily cut or ripped. This will help to ensure that the sterility of the container is kept intact after sterilization as the container is moved to storage or within the hospital in preparation for surgical use. Exemplary filter materials include, for example, nonwoven filter materials such as medical grade paper, polyolefin meltblown materials and nonwoven laminate materials such as laminates of spunbond materials and meltblown materials. These are materials that are stable in the presence of steam and heat as well as in the presence of ethylene oxide. Generally, gas permeable materials which may be used in the present disclosure are, as discussed above, permeable to water vapor and desirably have a minimum water vapor transmission rate (WVTR) of about 200 $g/m^2/16$ hours, calculated in accordance with ASTM Standard E96-80. Suitable medical grade paper includes, for example, AMCOR PLP reinforced coated paper available from AMCOR, Limited.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface.

As used herein "multilayer nonwoven laminate" means a laminate wherein some of the layers are spunbond and some meltblown such as a spunbond/meltblown/spunbond (SMS) laminate and others as disclosed in U.S. Pat. No. 4,041,203 to Brock et al., U.S. Pat. No. 5,169,706 to Collier, et al, U.S. Pat. No. 5,145,727 to Potts et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (6 to 400 gsm), or more particularly from about 0.75 to about 3 osy. Multilayer laminates may also have various numbers of meltblown layers or multiple spunbond layers in many different configurations and may include other materials like breathable films (F) or coform materials, e.g. SMMS, SM, SFS, etc.

The lid 30 and tray 40 may be constructed of an inexpensive material like a plastic polymer (e.g. polyolefin, polyester, PTFE, nylon, urethanes, copolymers and the like) or thin metal (e.g. aluminum, copper and alloys) and so may be disposable or single use. Alternatively, the lid and more desirably the tray, may be made from a more substantial material or thicker or heavier duty polymer or metal so that it may be reused a number of times. It is envisioned that the tray used in the practice of this disclosure will be reusable for as long as it is not physically distorted to the point where the rim cannot form a suitable barrier. It is also envisioned that the lid will most likely be a single use item made from polyethylene or polypropylene that will be recycled after use.

Desirably, the lid 30 and tray 40 may be formed of a substantially transparent material. Alternatively, the lid or tray may contain parts, sections or inserts that are substantially transparent. By "substantially transparent" what is meant is that a user may see through the material with the unaided eye under ambient light conditions sufficiently to distinguish between the items in the container. Accordingly, for purposes of the present disclosure "ambient light conditions" refers to light conditions of between about 500 lux (lx) and 2000 lx, more desirably, from about 750 lx to about 1500 lx as determined in io accordance with the British Standards Institution Code of Practice for Day-lighting, BS 8206 Part 1. Having at least a portion of the lid or tray being substantially transparent allows the contents of the container to be at least partially visible before and after sterilization and prior to removal of the lid. While the locking mechanism disclosed herein allows for opening of the container prior to sterilization as a way to check the contents of the container, it is also desirable to have a second method of checking the contents of the container without opening the container, even prior to sterilization. Making the lid, for example, from a transparent material allows for very easy inspection of the contents without opening the container. Should a more detailed inspection be necessary prior to sterilization, the lid can be removed from the tray and the instruments manually inspected or rearranged.

The lid and tray must be able to withstand exposure to steam, ethylene oxide, or other forms of sterilization without degradation. Desirably, the lid 30 and tray 40 may be made of a recyclable material such as, for example, a thermoplastic polymeric material as discussed in more detail above. The materials of the container should be able to withstand sterilization temperatures of from about 135° F. (59° C.) for some gas or plasma sterilization processes to about 300° F. (149° C.) for certain steam sterilization processes, without melting, bending, or losing strength. As an example of a particular process, the materials used for the lid and tray should be able to withstand steam sterilization temperatures ranging from about 266° F. (120° C.) to about 300° F. (149° C.) at least one time without melting, bending, losing strength or absorbing moisture. It is important that the materials not absorb moisture during steam sterilization so that the instruments are not wet and possibly slippery when it is time to use them. Should a wet instrument slip from a user's grasp and become unsterile, by for example, dropping to the floor, another instrument tray will be required to be used. The use of a second instrument tray of course increases surgical costs and increases the strain on hospital resources. Exemplary materials include polypropylene, polyethylene, polyesters, certain thermoplastic polyurethanes, olefinic copolymers and the like. The tray 40, as io mentioned above, is desirably made from a polymeric material since it is desirable that the tray 40 be transparent or that a portion of the liner be transparent, but thin metal materials may also be used if transparency is not required. Suitable metals include aluminum and copper and various alloys.

A reusable lock is used to secure the frame or tray 40 and the lid 30 together. By "reusable" is meant a lock that may be engaged and disengage without the use of destructive force and without damaging the lock elements to the point that they are incapable of being reused. In the first locking position the tray and lid are held together sufficiently tightly so that the container may be successfully sterilized and remain in a sterile condition after the sterilization process is complete. There are a number of factors that affect the maintenance of sterility, including the condition of the gasket and the filter, as noted above. The lock is important in this aspect as well since a poorly performing lock will allow the lid and tray to become loose or less well secured and allow microorganisms to infiltrate the container. The lock provided herein clearly engages the first and second locking elements and provides a firm and secure connection until a user desires to disconnect the lid and tray to check the contents or add or subtract items (prior to sterilization) or to open the container for use of the instruments contained therein (after sterilization).

A first locking element 80 may be located on a first piece (e.g. the lid 30 or tray 40) and has a hinge 84 adapted to releasably engage a second locking element 90 located on a second piece as well as to non-simultaneously, non-releasably engage a third locking element 86 located on the first piece. More particularly, the reusable lock includes a first locking element 80 that may form a portion of the lid 30 and a second locking element 90 that may form a portion of the tray 40 as shown in cross-section in FIG. 3A. When the lid 30 is mated to the tray 40 to seal the container, the first and second locking elements 80, 90 may be engaged into a releasable lock to secure the lid and tray together in a first lock position. That is, after being joined together, the first and second locking elements can be readily disengaged without damaging or destroying the lock and/or portions of the tray 40 or lid 30. The second locking element 90 may be formed substantially or completely out of a portion of the tray 40 and the first locking element 80 may be formed substantially or completely out of a portion of the lid 30. The first locking element is operated by manually applying pressure to the first locking element to urge it in the direction of the second locking element. The hinge portion of the first locking element allows the first locking element to move toward the second locking element (generally downwardly in the Figures) until it eventually contacts the second locking element. When the two components (the first and second locking elements) come into contact with one another, one or both of the components will slightly deform and allow the other to pass beyond an initial contact position. The components will then resume their initial un-deformed shapes and thus create a locking position. The lid and tray are held in a close connection with the barrier to microbial passage between them in place, and the container ready to be sterilized.

If it is necessary or desired to inspect the interior of the container once the first and second locking elements 80, 90 are engaged, they may be separated, released or disengaged. The means for separating the locking elements 80, 90 may be, for example, a hook, handle, flap, a tab, a pull, or grip, a finger slot or the like and combinations thereof. If a flap is used, the locking elements 80, 90 may be disengaged by applying manual force and pulling outwardly on the flap. The flap then rotates away from the second locking element as the hinge permits it to move in response to the manually applied force. The first and second locking elements will again slightly deform and allow the other element to pass beyond the point of initial contact and hingedly disengage, returning eventually to their initial positions if desired. This allows the user to separate the lid 30 and tray 40 to inspect the contents of the basket 50 or to add or subtract additional items to or from the basket 50.

Once the user is confident of the contents of the basket 50, the first and second locking elements 80, 90 can be engaged again (FIG. 3A) and the container 10 sterilized. In this embodiment, the first and second locking elements 80, 90 may be io engaged by pushing downwardly on the flap 82 until it engages the second locking element 90. The act of engaging the releasable lock components, i.e. mating feature 86 and flap 82, relies on initial spatial deflection of at least one element of a lock component, e.g. a bayonet tab 92 with a detent 94 (FIG. 4), against (at least) a mating element of the other lock component, followed by spatial re-deflection of the at least one element so that it 'catches' one or more elements of the other lock component. The detent 94 and mating component are adapted to be releasable by making the detent 94 relatively small so that the amount of force required to release it from the mating feature is concomitantly small.

Alternative methods of releasably connecting the first and second locking elements include, for example, the use of balls and sockets wherein a ball component will mate with a socket that is slightly smaller than the diameter of the ball. Like the tab and detent system, the application of manual force to urge the ball into the socket will deform one or both components and allow them to pass beyond one another to a first locking position. The ball or socket, desirably the ball, may be hingedly attached to, for example, the lid and the socket attached to the tray. Once they are engaged with one another, they may be separated, released or disengaged by the application of manual force to again deform the ball and or socket to allow the ball to come away from the socket and hingedly return to its initial position.

Another method of releasably connecting the first and second locking elements is through the use of a rotating hasp lock that engages a bar. In this embodiment, the rotating hasp may be placed on the lid using the hinge attachment to allow it to move toward the second locking element with the application of manual force. Unlike the tab and detent system, however, the hasp may be rotated to lock onto a bar on the tray, for example, without deformation of either part. Once they are engaged with one another, they may be separated, released or disengaged by the application of manual force to disengage the hasp from the bar and to hingedly return the hasp to its initial position. Other methods and features of making the releasable lock that are known to those skilled in the art may also be used, as this discussion is not meant to be exhaustive.

When it is desired to remove the sterilized components or items, the first and second locking elements 80, 90 may be disengaged and the flap 82 may be rotated upwardly around the hinge 84 until it engages the third or permanent locking element mating feature 86 in a second lock position that does not secure the lid 30 to the tray 40 (FIG. 3B). As discussed above, the first and second locking elements are usually, though not in all embodiments, deformed slightly in the process of disengagement. The application of manual force to hingedly move the first locking element away from the second locking element disengages the lock between the lid and the tray and allow the user to have access to the sterilized instruments.

Engaging the first lock element with the third locking element is a permanent connection that ensures that the lid and tray will not be reconnected after they have been disconnected after sterilization. This aspect of the disclosed device helps prevent a subsequent user from inadvertently using a non-sterile instrument. For example, if a first user of a lid and tray without the disclosed locking device were to open a sterile container and then reclose it using a releasable lock, a subsequent user would have no way to know that the container had been opened and potentially exposed to unsterile conditions. The provision of a non-releasable lock helps ensure that future users of the sterilized container will know that the container has been opened after sterilization and will enquire about the status of the instruments prior to using them.

The first locking element clearly cannot engage the second and third locking elements simultaneously as they are located on different items (e.g. lid and tray). The third locking element is located on the same item as the first locking element so that the tray and lid may be separated once the first and second locking elements are disengaged. The third locking element permanently holds the first locking element in place and, to do so, may also rely on a bayonet tab 88 with a detent 89 (FIG. 5), against (at least) a mating element of the other lock component, followed by spatial re-deflection of the at least one element so that it 'catches' one or more elements of the other lock component. The detent 89 and mating components may be adapted to be non-releasable by making the detent 89 relatively large so that the amount of force required to release it from the mating feature is concomitantly large. While it may be theoretically possible to release the first and third locking elements, the amount of force required is desirably beyond the ability of most users without mechanical assistance, e.g. a wrench or other tool. Should a user provide such an amount of force, either with his unaided hands or with a tool, at least one of the locking elements will be irreparably damaged and serve as a signal to any user that the sterility of the instruments in the container may be compromised.

As mentioned above, bar and socket and hasp and bar systems may be used to sufficient effect for the first and second locking elements. A third locking element for either system may be envisioned by making the socket or hasp, for example, sufficiently tight fitting that disengagement requires an amount of force that will result in damage to the components of the locking mechanism or perhaps to the container itself. Other methods and features of making the non-releasable lock that are known to those skilled in the art may also be used.

Another feature of the disclosed container lock is that after the first and third locking elements 80, 86 have been engaged, a space 96 that may be used as a handle is created. Once the lock is permanently engaged, the user's finger(s) may be inserted into the space 96 to lift the lid off of the liner and/or frame to allow access to the sterilized instruments. The space may be designed to be larger or smaller depending on the size of the first locking element by for example, lengthening or shortening the hinge 84 and moving the elements farther apart. Once the first locking element, e.g.; flap 82 and the permanent locking element 86 are engaged, they cannot be disengaged except through the use of a destructive amount of force, as mentioned above. The user may therefore be assured that the permanent lock will not disengage and the handle will exist permanently as well, allowing the user to manipulate the lid for disposal or preferably for recycling or for use in holding other items. The lid could be inverted, for example, and used to store items in the operating room during a surgical procedure. Since the inner surface of the lid is sterile, it may be used for the storage of instruments prior to use. It may also be used as a receptacle for used instruments or other items to be re-sterilized or disposed of.

While a single reusable lock may be used on a tray and lid, it is desirable to employ multiple reusable locks at various locations in securing the lid 30 and the tray 40 together. More desirably, at least one lock on either of the longer sides of the container 10 may be used. Since some sterilization containers can be quite large, a larger number of locks is desirable to help ensure that a gap does not develop in the barrier. Containers 10 are generally about 36 cm (14.25 inches) long by about 17 cm (6.85 in) wide by about 16 cm (6.25 in) in height. Another common size is 58 cm long (23 in) by 34 cm (13.5 in) wide by 16.5 cm (6.5 in) in height. Other sizes and dimensions of the container may be available or may be made. The lock may vary in size from quite small, e.g. a centimeter in length, to quite large, e.g. 10 cm or more. In the case of a large container, multiple large locks may deployed along each side. For example, for a 36 cm by 17 cm container, three 10 cm locks could be placed along each 36 cm side, with one in the center of the side and the others equally spaced between the center and the corners. Two slightly smaller locks could be located on each 17 cm long side. It should be noted that the locks deployed on the container need not be the same size as each other though for ease of manufacturing it is likely they would be.

As described above the hinge 84 is an element that allows the flap 82 to rotate. The hinge may be a conventional hinge having knuckles and a pin or, more desirably, may be a living hinge. Those skilled in the art will understand that living hinges are thin sections of material (e.g. plastic) that connect two segments of a part to keep them together and allow the part to be opened and closed, generally many times. Since the io lid as discussed herein is desirably disposable after a single use, a hinge that is reusable a large number of times is not necessary. The hinge should, however, be sufficiently robust as to allow the user to connect and disconnect the first and second locking elements at least a dozen times. A hinge design that cannot be reused at least a dozen times would likely have some embodiments that broke after just a first or second use, causing the user to question the efficacy of the disclosed locking container system generally. A hinge design that could be reused many times (e.g. hundreds of times) would be far more than required and would likely be prohibitively expensive to produce.

In an embodiment of the sterilization container it may be configured such that the second locking element 90 is incorporated in the rim of the tray 40 and the first locking element 80 is incorporated in a peripheral portion of the lid 30 that surrounds the central portion of the lid 30 and includes the lip. In such an embodiment, the peripheral portion of the lid 30 and the rim of the tray 40 may releasably engage into a reusable lock when the lid 30 is mated to the tray 40 to seal the container. The third locking element is incorporated in this embodiment into the lid 30. When engagement of the lid and tray is accomplished the barrier to microbial contamination is formed and the container may be sterilized. In this configuration the locks may be quite small so that the space 96 created when the first and third locking elements are engaged is also small and perhaps unusable as a handle. This embodiment may be advantageous however, for those situations where storage space in the hospital is at a premium, since this embodiment will require less space than other designs.

In yet another embodiment of the sterilization container it may be configured such that the second locking element is incorporated in the distal portions of the sides 46 of the tray 40 and includes the lip 42 of the tray 40, and the first locking element 80 is incorporated in a peripheral portion of the lid 30 that surrounds the central portion of the lid 30 and includes the rim 32 of the lid 30. The third locking element is incorporated into the lid 30. In this configuration the engagement of the first and third io locking elements provides a space that should be large enough to be used as a handle.

In still another embodiment of the sterilization container it may be configured such that the first locking element is incorporated onto the sides 46 of the tray 40 and the second locking element is incorporated in a peripheral portion of the lid 30 that surrounds the central portion of the lid 30 and includes the rim 32 of the lid 30. The third locking element is likewise incorporated into the sides 46 of the tray 40. In this configuration the space that is created by the mating of the first and third locking elements is located on the tray. The locating of only the second locking element on the lid in this embodiment allows the tray to be manually manipulated easily by a user through the use of the handle. Since the tray portion of the container is generally larger (deeper) than the lid portion, a user may find the tray with handles to be more useful after the instruments have been removed than the lid would be. Such a tray could be used for storage of used instruments or items to be disposed of and would have a lower likelihood of spillage since the tray generally has higher sides than the lid.

In another embodiment, the container may avoid the use of the tray 40 and instead use a reusable frame 100 with a disposable liner 110, as shown in FIG. 6. The disposable lid 30 and liner 110 may be used for only a single sterilization cycle or single use. The locking sterilization container 10 includes a reusable frame 100, a lid 30 with a permeable filter 34, and a liner 110 that is adapted to accept a standard hospital instrument basket 50. This embodiment is configured such that the second locking element 90 is incorporated in the rim of the frame 100 and the first locking element 80 is incorporated in a peripheral portion of the lid 30 that surrounds the central portion of the lid 30 and includes the lip. In such an embodiment, the peripheral portion of the lid 30 and the rim of the frame 100 may fixedly engage into a reusable lock when the lid 30 is mated to the frame 100 to seal the container. The third locking element is incorporated into the lid 30.

The container using a disposable liner, frame and lid may provide a better sterilization system than that using a solid tray. Since the liner is disposed of after each use, each liner is new when first used and the user can be assured that it does not harbor any microorganisms prior to sterilization. The user, e.g. the hospital, need only be concerned with the storage and maintenance of the reusable frames. The frames are relatively light weight and can be designed to nest together for storage. Since they are an open design, during storage they will not hold dirt or dust and any moisture that may be present on the frames will be removed by air circulation that passes freely through them. The liner should be made from a recyclable material such as a polyolefin (polypropylene, polyethylene) or other easy to reuse polymer.

In the use of the disclosed device, once the instruments are placed in the basket 50 and the basket 50 placed in the tray 40, the lid 30 is (releasably) locked onto the tray 40 prior to entering a sterilization chamber. Once the sterilization container 10 of the present disclosure containing the items to be sterilized is placed within the sterilization chamber, the sterilization chamber is closed and a gas sterilant such as steam or ethylene oxide is introduced into the container. The amount of time the items in the compartment are subjected to sterilization conditions depends on various factors, including the type of sterilizing media used, the number of medical instruments placed in the sterilization container as well as other factors. Those skilled in the art of sterilization will be able to determine the appropriate amount of time the sterilant should remain in the chamber based on these and other factors. The successfully sterilized containers are then removed from the chamber and stored or prepared for use. When the sterilized items are needed for surgery, the container 10 may be opened by disengaging the releasable lock(s), engaging the non-releasale lock(s) and opening the container 10 by separating the lid 30 and tray 40. The space created by the engaging of the non-releasable locks can create a handle for use by medical personnel for easy handling of the lid and/or tray.

While various patents have been incorporated herein by reference, to the extent there is any inconsistency between incorporated material and that of the written io specification, the written specification shall control. In addition, while the disclosure has been described in detail with respect to specific embodiments thereof, it will be apparent to those skilled in the art that various alterations, modifications and other changes may be made to the disclosure without departing from the spirit and scope of the present disclosure. It is therefore intended that the claims cover all such modifications, alterations and other changes encompassed by the appended claims.

I claim:

1. A locking container for sterilizing and preserving surgical materials in a sterilized condition, the container comprising:
    a lid comprising a central portion and a continuous lip, the lid comprising a permeable filter providing a path for a sterilant to enter the container from outside the container and for maintaining aseptic conditions inside the container after sterilization;
    a tray comprising a base, sides and a continuous tray rim, the tray adapted to receive a basket for containing surgical instruments such that the lid lip and tray rim together form a barrier to inhibit the passage of microorganisms into the chamber, and;
    a lock having a hinge for releasably securing the lid and tray together in a first lock position and a non-releasably locked second lock position that does not secure said lid to said tray.

2. The locking container of claim 1 wherein said lock comprises a bayonet tab with a detent and a mating component.

3. The container of claim 1 wherein said lock may be non-releasably locked to the lid.

4. The container of claim 1, wherein the lid is made from a material selected from the group consisting of polypropylene, polyethylene, polyesters, thermoplastic polyurethanes, olefinic copolymers, aluminum, copper and various alloys.

5. The container of claim 1 wherein said tray is disposable and is made from aluminum.

6. The container of claim 1, wherein the rim of the lid includes a material which is heat activated during steam sterilization to secure the lid and the tray.

7. The container of claim 6 wherein said material for inclusion in the rim includes hot melt adhesives made from polyolefins, block copolymers, resins, waxes and combinations thereof, that have a melting point below 270° F. (132° C.).

8. The container of claim 1, wherein the lid has a gas permeable filter is in the central portion of the lid.

9. The container of claim 8, wherein the filter material is selected from the group consisting of medical grade paper, polyolefin meltblown materials and nonwoven laminate materials such as laminates of spunbond materials and meltblown materials.

10. The container of claim 9 wherein said gas permeable filter material is permeable to water vapor and has a minimum water vapor transmission rate (WVTR) of about 200 g/m$^2$/16 hours, calculated in accordance with ASTM Standard E96-80.

* * * * *